United States Patent
Chen et al.

(10) Patent No.: US 8,301,219 B2
(45) Date of Patent: Oct. 30, 2012

(54) PATIENT MONITORING SYSTEMS AND METHODS

(75) Inventors: Fred Chen, Boston, MA (US); Henry Wu, Brighton, MA (US); Pei-Lan Hsu, Lakewood, CA (US); Brad Stronger, Cambridge, MA (US); Hongshen Ma, Cambridge, MA (US); Robert L. Sheridan, Lexington, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 665 days.

(21) Appl. No.: 12/500,031

(22) Filed: Jul. 9, 2009

(65) Prior Publication Data

US 2010/0041975 A1 Feb. 18, 2010

Related U.S. Application Data

(60) Provisional application No. 61/081,164, filed on Jul. 16, 2008.

(51) Int. Cl.
*A61B 5/04* (2006.01)
*A61B 5/0428* (2006.01)

(52) U.S. Cl. .................. 600/393; 600/382; 600/509

(58) Field of Classification Search .............. 600/393, 600/395, 382, 372, 509
See application file for complete search history.

(56) References Cited

U.S. PATENT DOCUMENTS

| | | |
|---|---|---|
| 3,888,240 A | 6/1975 | Reinhold, Jr. et al. |
| 3,926,177 A | 12/1975 | Hardway, Jr. et al. |
| 4,082,086 A | 4/1978 | Page et al. |
| 4,736,752 A * | 4/1988 | Munck et al. ............... 607/152 |
| 4,889,123 A | 12/1989 | Lee |
| 5,137,033 A | 8/1992 | Norton |
| 5,184,620 A | 2/1993 | Cudahy et al. |
| 5,224,479 A | 7/1993 | Sekine |

(Continued)

FOREIGN PATENT DOCUMENTS

GB 2356934 A 6/2001

(Continued)

OTHER PUBLICATIONS

A. Ueno, et al. "Capacitive Sensing of Electrocardiographic Potential Through Cloth From the Dorsal Surface of the Body in a Supine Position: A Preliminary Study," IEEE Transactions on Biomedical Engineering, vol. 54, No. 4. Apr. 2007.

(Continued)

*Primary Examiner* — Lee S Cohen
*Assistant Examiner* — Erin M Cardinal
(74) *Attorney, Agent, or Firm* — Nutter McClennen & Fish LLP

(57) ABSTRACT

Various systems and methods are provided for monitoring patient physiological data without the need for adhesives or wires to be connected to a patient. The system is also fully functional without the need for manipulation or intervention by a care provider or medical personnel. In particular, the system can include a pad having a plurality of electrical contacts or electrodes formed thereon in a predetermined pattern. The electrodes can be configured to sense electrical signals produced by a patient's body. A controller in communication with the electrodes can be configured to select and process signals from the electrodes and send the information derived from the electrical signals to an output device for displaying resulting physiological data so that the patient can be monitored.

20 Claims, 8 Drawing Sheets

U.S. PATENT DOCUMENTS

| | | | |
|---|---|---|---|
| 5,257,631 A | 11/1993 | Wilk | |
| 5,353,793 A | 10/1994 | Bornn | |
| 5,882,300 A | 3/1999 | Malinouskas et al. | |
| 5,989,409 A * | 11/1999 | Kurnik et al. | 205/792 |
| 6,047,203 A | 4/2000 | Sackner et al. | |
| 6,073,039 A * | 6/2000 | Berson | 600/372 |
| 6,253,103 B1 * | 6/2001 | Baura | 600/547 |
| 6,408,200 B1 | 6/2002 | Takashina | |
| 6,564,079 B1 | 5/2003 | Cory et al. | |
| 6,605,046 B1 | 8/2003 | Del Mar | |
| 6,727,445 B2 | 4/2004 | Cullinan et al. | |
| 6,840,907 B1 * | 1/2005 | Brydon | 600/534 |
| 6,847,301 B1 | 1/2005 | Olson | |
| 6,912,414 B2 | 6/2005 | Tong | |
| 6,973,344 B2 * | 12/2005 | Finneran et al. | 600/393 |
| 6,984,207 B1 | 1/2006 | Sullivan et al. | |
| 7,245,956 B2 | 7/2007 | Matthews et al. | |
| 7,250,547 B1 | 7/2007 | Hofmeister et al. | |
| 7,304,580 B2 | 12/2007 | Sullivan et al. | |
| 7,319,386 B2 | 1/2008 | Collins, Jr. et al. | |
| 2002/0067273 A1 | 6/2002 | Jaques et al. | |
| 2003/0045804 A1 | 3/2003 | Brodnick | |
| 2003/0109905 A1 | 6/2003 | Mok et al. | |
| 2003/0187363 A1 | 10/2003 | Alroy | |
| 2005/0038489 A1 * | 2/2005 | Grill | 607/116 |
| 2005/0049515 A1 | 3/2005 | Misczynski et al. | |
| 2005/0113703 A1 | 5/2005 | Farringdon et al. | |
| 2006/0015027 A1 * | 1/2006 | Matthews et al. | 600/393 |
| 2006/0173367 A1 | 8/2006 | Stuart et al. | |
| 2007/0060802 A1 | 3/2007 | Ghevondian et al. | |
| 2007/0142715 A1 | 6/2007 | Banet et al. | |
| 2007/0156031 A1 | 7/2007 | Sullivan et al. | |
| 2007/0208260 A1 | 9/2007 | Afonso | |
| 2008/0015454 A1 | 1/2008 | Gal | |
| 2008/0039904 A1 * | 2/2008 | Bulkes et al. | 607/62 |
| 2008/0064970 A1 | 3/2008 | Montplaisir | |
| 2008/0183063 A1 * | 7/2008 | Tang et al. | 600/382 |

FOREIGN PATENT DOCUMENTS

| | | |
|---|---|---|
| IN | 1325/CHE2005 | 12/2007 |
| JP | 8140947 A | 6/1996 |
| WO | 0074564 A1 | 12/2000 |

OTHER PUBLICATIONS

A.S. Sezen, S. Sivaramakrishnan, S. Hur, R. Rajamani, W. Robbins, and B.J. Nelson. "Passive Wireless MEMS Microphones for Biomedical Applications," Journal of Biomechanical Engineering, vol. 127, Issue 6, pp. 1030-1034, 2005.

Atkielski, Anthony. "Sinus Rhythm Labels," Jan. 13, 2007. Accessed: Dec. 14, 2007. <http://en.wikipedia.org>.

Cardiac Science, Inc., "University of Michigan to Compare Effectiveness of Cardiac Science Powerheart® CRM• Bedside Monitor-Defibrillator With Traditional 'Code Blue' In-Hospital Emergency Response Protocol; Poor In-Hospital Cardiac Arrest Mortality Rates Prompt New Clinical Study to Support New Standard of Care.", Mar. 24, 2005.

Chulsung Park and Pai H. Chou, Ying Bai, Robert Matthews, and Andrew Hibbs. "An Ultra-Wearable, Wireless, Low Power ECG Monitoring System," In Proc. IEEE BIOCAs, Nov. 29-Dec. 1, 2006. The British Library, London. Available HTTP://WWW.ECE.UCI.EDU/~CHOU/BIOCAS06-ECG.PDF.

F. Axisa, A. Dittmar, and G. Delhomme. "Smart Clothes for the Monitoring in Real Time and Conditions of Physiological, Emotional, and Sensorial Reactions of Human," Proceedings of the 25th Annual International Conference of the IEEE EMBS. Sep. 17-21, 2003.

Fred Chen, Henry Wu, Pei-Lan Hsu, Brad Stronger, Robert Sheridan, and Hongshen Ma, "SmartPad: A Wireless, Adhesive-Electrode-Free, Autonomous ECG Acquisition System," 30th Annual International IEEE EMBS Conference, Apr. 6, 2008.

Fulford-Jones, T.R.F.; Gu-Yeon Wei; Welsh, M., "A Portable, Low-Power, Wireless Two-Lead EKG System," Engineering in Medicine and Biology Society, 2004. EMBC 2004. Conference Proceedings. 26th Annual International Conference of the IEEE vol. 1, 2004 pp. 2141-2144 vol. 3.

Harland, C.J., et al., "Electrical Potential Probes—New Directions in the Remote Sensing of the Human Body," Measurement Science and Technology, 2002, vol. 13, p. 163-169.

Ishijima, M., "Monitoring of Electrocardiograms in Bed Without Utilizing Body Surface Electrodes" Biomedical Engineering, IEEE, vol. 40, Issue 6, Jun. 1993, pp. 593-594.

J.W. Weigold; T.J. Brosnihan; J. Bergeron; X. Zhang, "A MEMS Condenser Microphone for Consumer Applications," Micro Electro Mechanical Systems, 2006. MEMS 2006 Istanbul. 19th IEEE International Conference on , vol., No., pp. 86-89, 2006.

Jacobs, J.L., "Characterization of a Novel Heart and Respiratory Rate Sensor" Engineering in Medicine and Biology Society, 2004, IEMBS apos;04. 26th Annual International Conference of the IEEE, vol. 1, Issue 1-5, Sep. 2004, pp. 2223-2226, vol. 3.

Kearney, Kenneth; Thomas, Chris; McAdams, Eric, "Quantification of Motion Artifact in ECG Electrode Design," Engineering in Medicine and Biology Society, 2007. EMBS 2007. 29th Annual International Conference of the IEEE, pp. 1533-1536, Aug. 22-26, 2007.

Kohler, B.-U.; Hennig, C.; Orglmeister, R. "The principles of software QRS detection", Engineering in Medicine and Biology Magazine, IEEE vol. 21, Issue 1, Jan.-Feb. 2002 pp. 42-57.

Linz, Torsten, et al, "Fully Integrated EKG Shirt Based on Embroidered Electrical Interconnections With Conductive Yarn and Miniaturezed Flexible Electronics," Proceeding of the International Workshop on Wearable and Implantable Body Sensor Networks, 2006.

O. Abdel-Alim, et.al. "Heart Diseases Diagnosis Using Heart Sounds." Nineteenth National Radio Conference. Alexandria, Egypt. Mar. 19-21, 2002.

Oberg, T; "A Circuit for Contact Monitoring in Electrocardiography", IEEE Transactions on Biomedical Engineering, vol. BME-29, May 1982 pp. 361-364.

S. Borromeo, et al. "A Reconfigurable, Wearable, Wireless ECG System," Proceedings of the 29th Annual International Conference of the IEEE EMBS. Aug. 23-26, 2007.

Scanlon, M.V., "Acoustic Sensor Pad for Physiological Monitoring," Proceedings of the 19th Annual International Conference of the IEEE Engineering in Medicine and Biology Society, Oct. 1997.

Scanlon, M.V., "Acoustically Monitor Physiology During Sleep and Activity," Proceedings of the First Joint BMES/EMBS Conference, Oct. 1999.

The Innovative Technology, "The LifeShirt® Technology Brings Gold-Standard Monitoring Technology Into the Real-World Environment" Vivometrics 2007.

Vivometrics® Clinical Trials, "The LifeShirt® System" (no date).

W. Myint, B. Dillard. "An Electronic Stethoscope With Diagnosing Capability." IEEE 2001, p. 133. (0-7803-666 1 -1/01).

Y.G. Lim, K.K. Kim, and K.S. Park. "ECG Recording on a Bed During Sleep Without Direct Skin-Contact," IEEE Transactions on Biomedical Engineering, vol. 54, No. 4. Apr. 2007.

* cited by examiner

PATIENT MONITORING SYSTEMS AND METHODS

CROSS REFERENCE TO RELATED APPLICATIONS

The present application claims priority to U.S. Provisional Application No. 61/081,164 filed on Jul. 16, 2008 and entitled "Patient Monitoring Systems and Methods," which is hereby incorporated by reference in its entirety.

STATEMENT REGARDING FEDERALLY SPONSORED RESEARCH

This invention was made with government support under grant number DAMD17-02-2-0006 awarded by the Army. The government has certain rights in the invention.

FIELD OF THE INVENTION

The present invention relates to systems and methods for monitoring a patient's physiological data.

BACKGROUND OF THE INVENTION

The ability to measure a human's physiological signals is vital in monitoring, evaluating, and diagnosing the physiological status and health of an individual. Parameters such as heart electrical activity, physiological sounds, heart rate, oxygen saturation, respiration rate, blood pressure, and body temperature can all provide critical information about an individual's health. For example, an electrocardiogram, commonly referred to as an EKG or ECG, is a tool that health care providers use to monitor the bioelectrical activity of the heart. As the heart contracts to pump blood throughout the body, it enters various stages of depolarization and repolarization. These stages of depolarization and repolarization correspond to the contraction and relaxation of different areas within the heart. By measuring electrical signals associated with each heartbeat, cardiologists are able to identify abnormalities that exist in a patient's cardiac cycle.

In clinic settings, such as an ambulance, an operating room, and an intensive care unit, physiological parameters relating to a patient's vital signs are displayed for care providers so that the patient can be easily monitored. Physiological parameters such an ECG are conventionally measured using gel-coated electrodes adhered directly to a patient's skin by medical personnel and require medical personnel to actively participate in the measurement. The large number of wires associated with the electrodes and other measurement devices, however, can severely inhibit a medical team's access to the patient and can slow response time. Often, electrode adhesives fail if the skin is burned, bloody, or otherwise traumatized. Medical personnel may need to resort to placing electrodes and other measuring devices on a patient's back, legs, and in other sub-optimal locations due to problems with the standard placement locations.

Previous work in developing alternative bioelectric sensing systems, such as ECG systems, has primarily focused on enabling low cost mobile monitoring solutions or improving the accuracy and reliability of ECG signals through noise reduction or electrode design. Many low cost home monitoring devices, for example, primarily provide heart rate readings without real time ECG signals as would be needed in a clinical setting. Current higher end systems still rely on "sticky pads" connected by a cable to make contact to the patient. The solutions that transmit bioelectric signals wirelessly to display machines also rely on using several sticky pads to make contact to the patient. Additionally, all current approaches require a conscious effort on the part of medical personnel to attach electrodes to a patient and/or to position a sensing device in a specific location next to a patient so that physiological data can be monitored and displayed. There is therefore a need for systems and methods that can provide reliable monitoring of a patient's physiological parameters without requiring electrodes to be adhered to a patient, without the use of wires attached to the patient, or even without medical personnel assistance.

SUMMARY OF THE INVENTION

The present invention generally provides systems for monitoring patient physiological data and can include a pad having a plurality of electrical contacts formed thereon in a predetermined pattern. The electrical contacts can be configured to sense electrical signals produced by a patient's body. In one embodiment, a controller is provided in communication with the electrical contacts that can be configured to select at least two electrical contacts, each sensing a processable electrical signal, and to process a differential signal derived from the processable signals. An output device can also be included and can be in communication with the controller for displaying the patient's physiological data based on information processed by the controller. While the controller can be configured to perform various functions, in one embodiment, the controller is configured to monitor the plurality of electrical contacts and to select from among the electrical contacts different electrical contacts as needed to optimize the physiological data.

The plurality of electrical contacts can generally be formed from strips of conductive material that can be disposed on the pad in desired locations or in a predetermined configuration. For example, in one embodiment, the strips of conductive material are formed into two mirrored sets of nested L-shaped configurations. The strips of conductive material can be formed of any suitable material known in the art, and in one exemplary embodiment, the strips are formed from Nickel/Copper polyester fabric and/or from a cloth fabric having conductive fibers therein. At least one of the plurality of electrical contacts can be a devoted active ground configured to enable removal of 60 Hz noise from the signal processed by the controller. In one embodiment, the plurality of electrical contacts can be configured to sense electrical signals through a patient's skin to produce physiological data regardless of patient size or patient position on the pad. In other embodiments, the electrical signals sensed by the plurality of electrical contacts are electrocardiograph signals and physiological data displayed by the output device is an electrocardiograph.

The controller can have various electronic circuitry as needed and can include a multiplexing network, at least one amplifier, at least one filter, and at least one microprocessor. In one exemplary embodiment, the controller is battery operated and the output device can be configured to communicate with the controller wirelessly. The pad can be at least one of a gurney pad, a sheet, a warming blanket, and a hospital gown.

In another exemplary embodiment, a system for monitoring patient physiological data is provided and can include a pad having an array of electrodes formed thereon in a predetermined configuration. The pad can be configured to be positioned adjacent to a patient's skin, and a processor in communication with electrical contacts on the pad can be configured to select at least two electrodes from the array of electrodes, to process electrical signals received from the two electrodes, and to generate physiological data derived from the electrical signals. The processor can be further configured to periodically monitor signal strength sensed by the electrodes of the array and to actively change the selected electrodes to maintain optimization of physiological data.

In one embodiment, the array of electrodes can be strips of conductive tape that are formed into mirrored sets of nested L-shaped configurations. The strips of conductive tape can be formed from Nickel/Copper polyester fabric and/or a fabric cloth having conductive fibers. At least one of the array of electrodes can be a devoted active ground configured to enable removal of 60 Hz ambient noise. The electrodes can be configured to sense electrical signals through a patient's skin to produce physiological data regardless of patient size or patient position on the pad. In one exemplary embodiment, data generated by the processor can include electrocardiograph data.

Methods for monitoring a patient's physiological data are also provided and can include providing a pad having a plurality of electrical contacts formed thereon, positioning the pad adjacent to a patient such that at least some of the plurality of electrical contacts can sense electrical signals through the patient's skin, processing electrical signals received from the plurality of electrical contacts, selecting at least two electrical contacts from the plurality of electrical contacts based on the strength and quality of the electrical signals processed, and outputting the information derived from the selected electrical contacts such that a patient's physiological data can be monitored. In one embodiment, the step of processing electrical signals from the electrical contacts can include determining whether or not a patient is in contact with electrical contacts and assessing the quality of acquired electrical signals. In other embodiments, the step of positioning the pad adjacent to a patient can include positioning a patient in any orientation on or under the pad. The step of outputting the information derived from the selected electrical contacts can include outputting data relating to at least one of blood pressure, electrocardiogram, heart rate, oxygen saturation, respiration rate, and body temperature.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
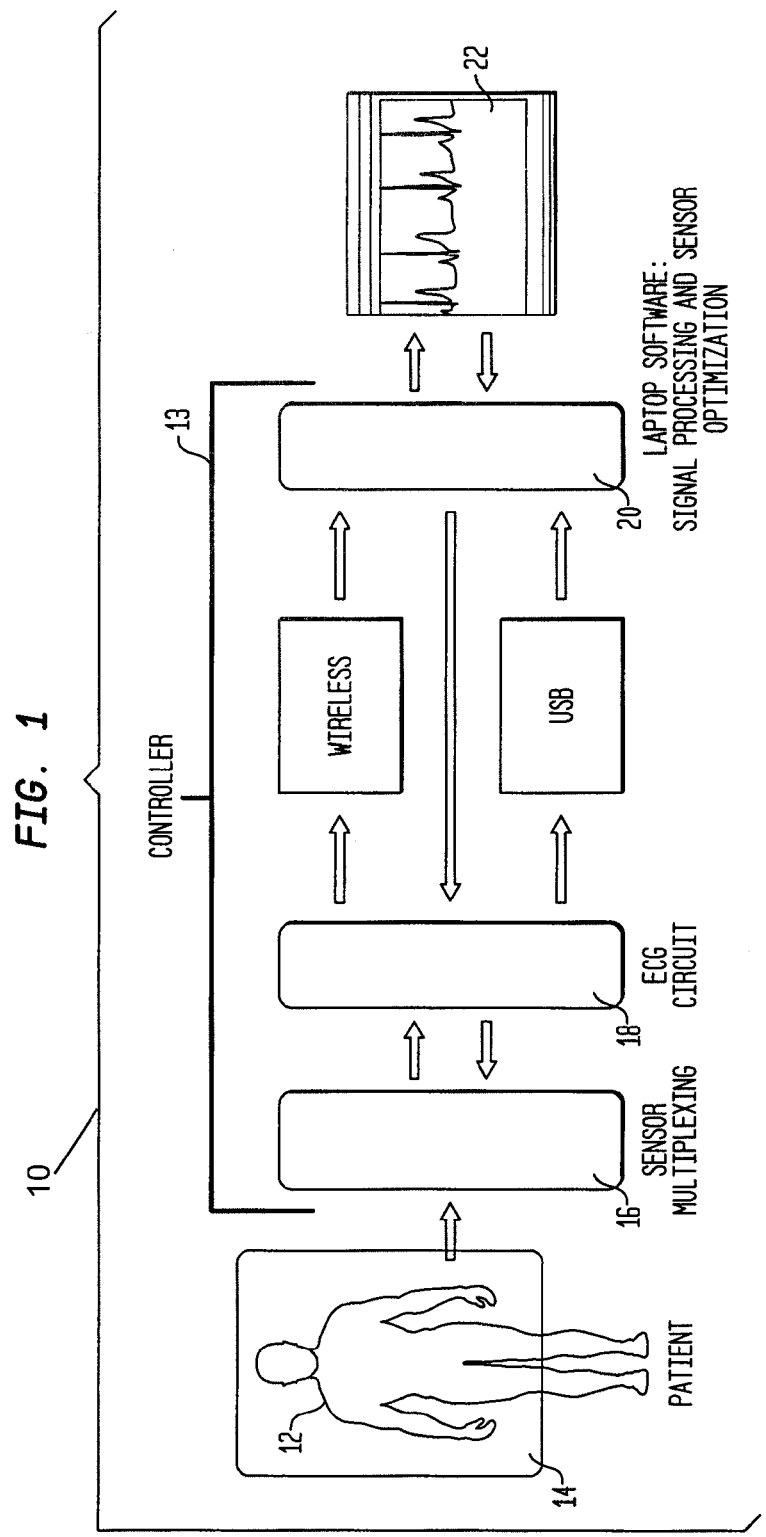
FIG. 1 is a representation of an exemplary system for monitoring a patient's physiological data.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides systems and methods for monitoring patient physiological data without the need for adhesives or wires to be connected to a patient. The system is also fully functional without the need for manipulation or intervention by a care provider or medical personnel. In particular, the system can include a pad having a plurality of electrical contacts or electrodes formed thereon in a predetermined pattern. The electrodes can be configured to sense electrical signals produced by a patient's body. A controller in communication with the electrodes can be configured to select and process signals from the electrodes and send the information derived from the electrical signals to an output device for displaying resulting physiological data so that the patient can be monitored.

The systems and methods described herein are particularly advantageous for use with patients having injured or traumatized skin, for example, burn victims, as there is no need for electrodes or wires to be adhered to skin that may already be traumatized. In addition, the systems and methods provided can also be used effectively with adults, young children, and infants alike that may not have available space for electrodes on their bodies due to injuries, surgical dressings, or other monitoring equipment. A patient need only to lay on or be covered by the pad, in any position, for the electrodes to sense the required signals to produce a display of the patient's physiological data.

Any type of physiological data can be measured and monitored as needed using a system of the invention. One particularly advantageous use for the systems and methods described herein is in the measurement and monitoring of a patient's electrocardiogram or ECG. In addition to an ECG, other physiological parameters can be monitored in the same or similar manner, including, but not limited to, physiological sounds measured using a stethoscope disposed in or on the pad; heart rate; oxygen saturation using pulse oximetry; respiration rate measured using accelerometers, microphones, or impedance plethysmography positioned on the pad; neurological activity using electrodes disposed on the pad; blood pressure; and body temperature using various temperature sensors studded throughout the pad. A person skilled in the art will appreciate that any number of physiological parameters and patient vital signs can be measured and monitored using the systems and methods described herein. The system will be further described herein in reference to obtaining patient ECG data, but it will be appreciated by those skilled in the art that all of the systems and methods described apply in the same or similar manners to the monitoring of other types of physiological parameters.

An overview of an exemplary system 10 for measuring and monitoring an ECG signal is provided and illustrated in FIG. 1. As shown, a patient 12 is positioned adjacent to a pad 14. Electrodes on the pad (not shown) can sense, for example, the electrical signals caused by the beating of the patient's heart, and a controller 13 can multiplex, amplify, filter, and further process these signals to send to a remote output device 22 for monitoring by medical personnel. In particular, two electrodes can be multiplexed from the pad 14 using the multiplexing network 16 and sent into amplification and filtering stages as illustrated by box 18, along with a common ground signal taken from the pad 14. An amplified and filtered ECG signal is then passed to a microprocessor 20 for analog-to-digital conversion and transmission to the remote output device 22 via any suitable connection, including by wireless and/or USB transmission. The resulting ECG data can be displayed by the output device 22.

Figure 2:
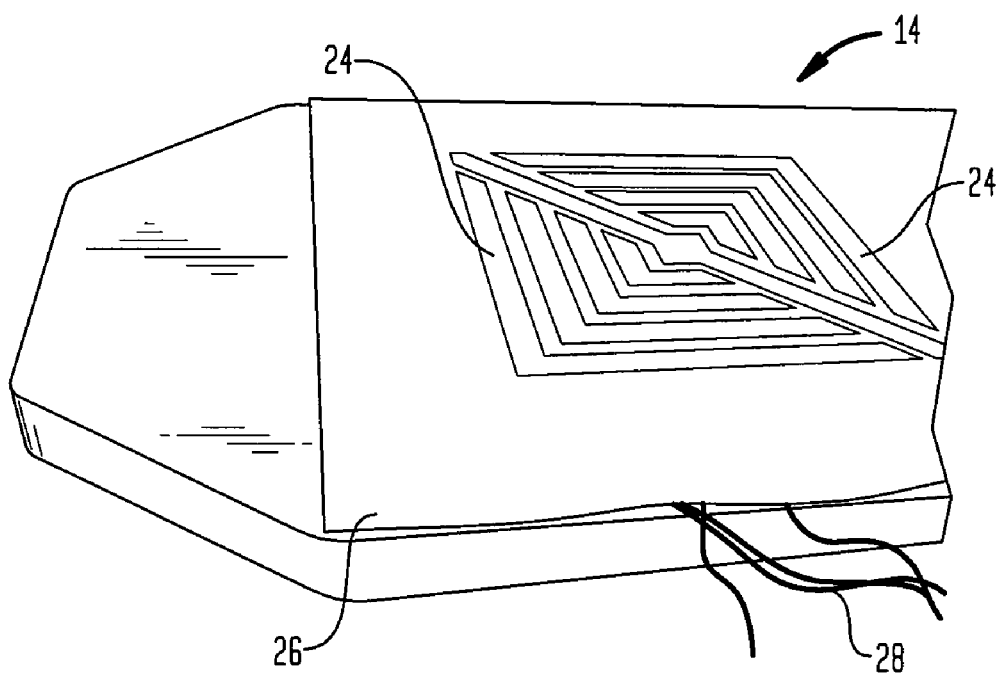
FIG. 2 is a perspective view of an exemplary embodiment of a pad having electrodes formed thereon of the system of FIG. 1.

While the system 10 can have many configurations, in one exemplary embodiment shown in FIG. 2, the system 10 can include the pad 14 having electrodes 24 formed thereon that can be placed adjacent to a patient's skin. The pad 14 can have a soft, compressible layer that is flexible and will not be irritating to a patient's skin. The pad 14 can also include a thin liner 26 that can be placed on top of the compressible layer and that is configured to have the electrodes 24 formed thereon. The electrodes 24 can be attached to the thin liner 26 in a predetermined configuration as described below and a number of electrical leads 28 can extend from the electrodes 24 between the thin liner 26 and the compressible layer to connect the electrodes to the controller 13. Alternatively, the compressible layer and thin liner can be a single piece of flexible material and the electrodes 24 can be attached directly to the flexible material.

While the pad 14 can be made into any shape or form as needed in specific applications, in one exemplary embodiment, the pad 14 can have a rectangular shape that is large enough to receive the upper torso and/or full body of a patient, and it should be suitable for placement in a hospital bed, an ambulance bed, or on a stretcher or gurney. Alternatively, the bed, stretcher, or gurney can have the pad 14 formed integrally therewith. The pad 14 can also have any thickness as needed. For example, the pad 14 can have a thickness sufficient to form a compressible cushion that will compress under a patient's weight and conform to a patient's body. Alternatively, the pad 14 can be thin enough to placed over an existing bed, stretcher, or gurney pad and/or to form a sheet that can be draped over a patient's body. In one embodiment, the pad 14 can be formed into a warming blanket for use in surgical applications and/or for in-home care applications. The pad 14 can also be formed into a wearable element such as a hospital gown or other piece of clothing. In all of the embodiments described herein, the pad 14 can be reusable or disposable. In addition, in all of the embodiments described herein, the pad 14 and associated components can be mobile or portable, for example in the form of a foldable gurney, for use in a military field situation or emergency response situation, as well as in any other situation that could benefit from a portable monitoring device. A person skilled in the art will appreciate the variety of additional shapes and forms the pad 14 can take.

The pad 14, including the compressible layer and the liner 26, can be made of various materials, but a light and resilient material can optimize comfort and ease of use. In an exemplary embodiment, the pad 14 is made from materials commonly used in fabric and textile applications that are biocompatible and nonconductive. For example, the pad 14 can be made from elastomeric yarns (such as spandex) and/or comfort yarns (such as nylon, polyester, and cotton). Any combination of materials can be used as necessary to maximize comfort and ease of use for the patient, as well as to provide ease of cleaning if required. In one embodiment, the compressible layer of the pad 14 can be an Universal Stretcher Pad with Pressure Displacing Foam™, commercially available from Aadco Medical. The thin liner 26 can be made from ⅛-inch thick silicon foam that is placed on top of the compressible layer. The pad 14 can also be configured to be used for extended lengths of time by a patient or it can be configured to be used only at specific times or only once as needed.

Figure 3:
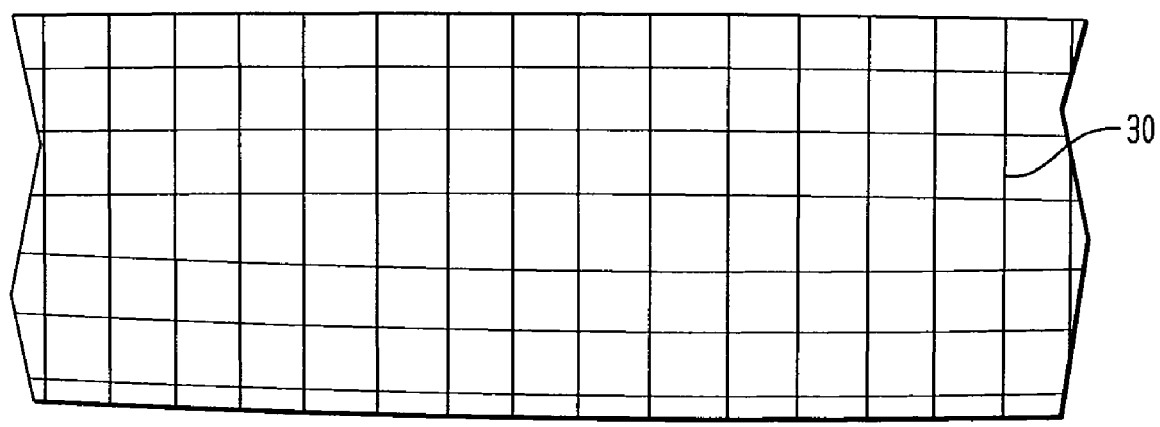
FIG. 3 is a top view of an exemplary electrode formed from conductive tape for use in the system of FIG. 1.

In one embodiment, the electrodes 24 formed on the pad 14 require direct contact to a patient's skin in order to sense electrical signals within a patient's body. As such, the electrodes 24 can be formed of a conductive material that is soft and flexible enough to be positioned adjacent to a patient's skin. In one embodiment, the electrodes 24 can have an adhesive on one side in order to allow adhesion to the pad 14, or they can be joined to pad by other techniques including by being sewn thereto. The electrodes 24 can also be configured to withstand corrosion so that they are compatible with a saline environment, such as a patient's burned and/or bloody skin. In one exemplary embodiment shown in FIG. 3, the electrodes 24 can be made of a nickel on copper-plated polyester fabric tape 30 that is coated on one side with an adhesive. Alternatively, the tape 30 can be formed of a cloth fabric having conductive fibers formed therein and therethough. The tape 30 can be generally rectangular in shape having a length that can be cut to specified lengths as needed to form electrodes and a width that is generally narrower than the length. As will be appreciated by those skilled in the art, the tape 30 can be cut to any length such that a square is formed or such that the width is larger than the length. The tape 30 is preferably a fabric that has no sharp edges and feels virtually indistinguishable in texture to the pad 14. Alternatively, the electrodes 24 can be made of traditional metal wire, non-fabric tape, or any other material known in the art that is conductive and able to sense electrical signals through a patient's skin.

In general, the electrodes 24 can be formed in any variety of shapes and configurations on the pad 14 as long as the configuration allows for a differential measurement to be taken across a patient's heart, in the case of measuring and monitoring an ECG signal. By taking a differential measurement across two static points that span the heart, it is possible to record the projection of these electrical vectors onto the vector between two static points to produce the characteristic waveform associated with a single cardiac cycle, as will be appreciated by those skilled in the art. Accordingly, while there can be any number of electrodes 24 formed onto the pad 14, only two electrodes 24 are needed to make a measurement in a two-lead system. A third electrical contact can be included to form a three-lead system in which the third electrical contact serves as a common ground. In another embodiment, a twelve-lead system is provided in which ten electrodes are used to allow monitoring of electrical vectors projected onto a larger choice of lead vectors. The description of systems and methods herein will refer to the three-lead system, but a person skilled in the art will appreciate that all of the systems and methods described can be expanded to include any lead system, including the twelve-lead system, as well as the simpler two-lead system.

Figure 4A:
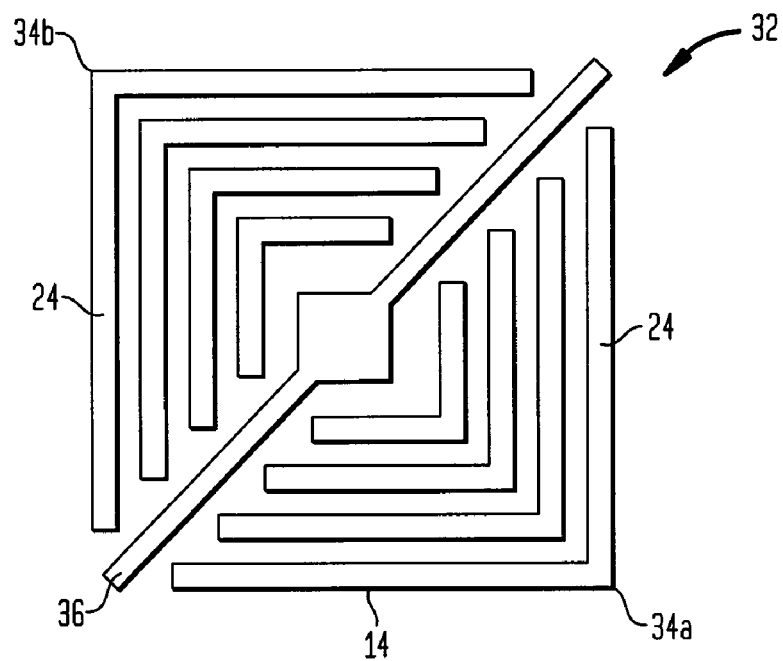
FIG. 4A is a top view of one embodiment of an electrode configuration for use in the system of FIG. 1.
Figure 4B:
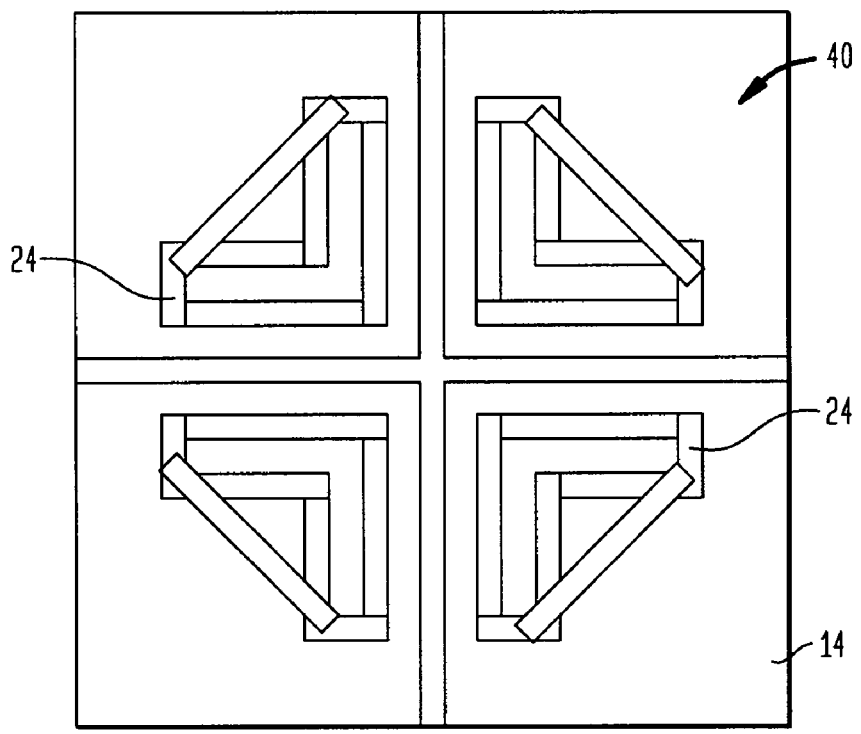
FIG. 4B is a top view of another embodiment of an electrode configuration for use in the system of FIG. 1.

Referring now to FIGS. 4A-4C, an array or plurality of electrical contacts or electrodes 24 can be formed on the pad 14 in any configuration that allows a differential measurement to be taken across the heart and that is not dependent on patient position on or under the pad 14. A patient, whether a full grown adult or a child, can thus lay on the pad 14 in any position and a measurement can still be obtained. In one embodiment shown in FIG. 4A, the array of electrodes 24 can be formed in a nested L-shaped configuration 32. Four of the electrodes 24 are formed in nested Ls on one corner of the pad 34a, while a mirror image of the four electrodes 24 is formed on an opposite corner 34b of the pad 14 for a total of eight L-shaped electrodes. A single grounding electrode 36 is positioned in the center of the eight electrodes 24, although it can have any position on the pad 14, and acts as a devoted common ground for the pad 14. In another embodiment, shown in FIG. 4B, the electrodes 24 are formed in a four triangle grid 40. In still another embodiment, the electrodes 24 can be formed in a grid configuration such that the entire pad 14 is studded with electrodes 24. A person skilled in the art will appreciate the various electrode configurations possible.

Figure 5:
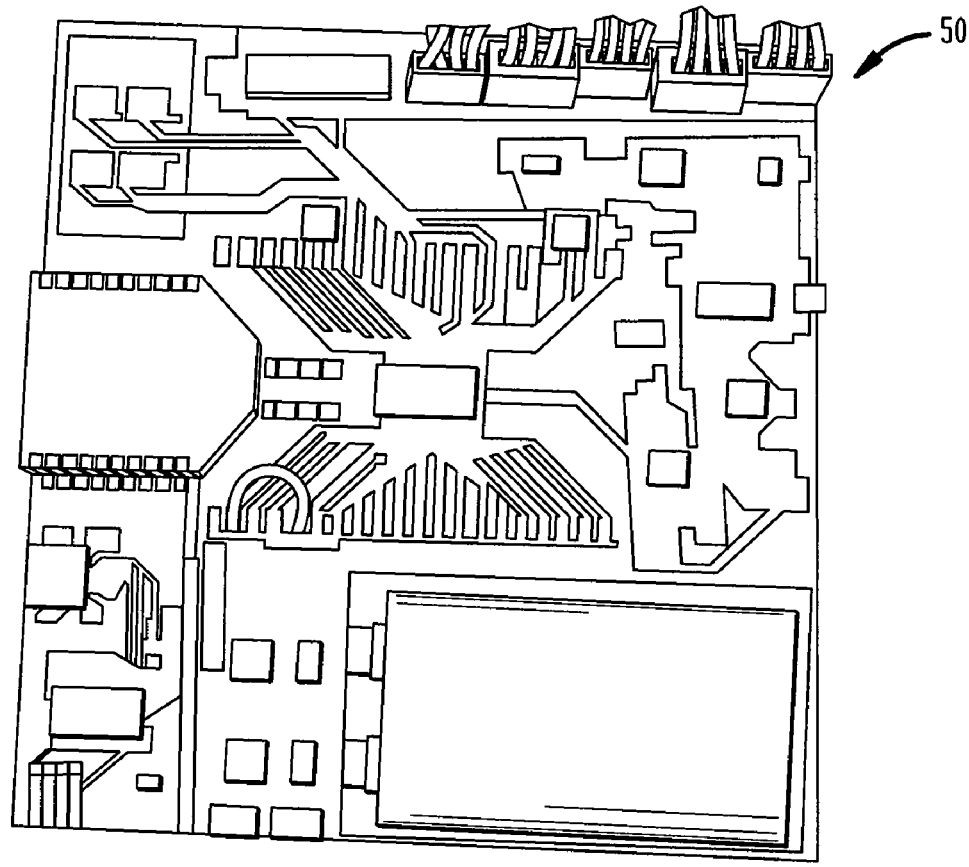
FIG. 5 is a top view of an exemplary circuit board for use with the system of FIG. 1.

To form the various configurations, sections of conductive fabric tape can be adhered together using the adhesive formed on one side, as described above. Thus, no soldering is necessary to form connections. If electrical wire or non-fabric electrical tape is used as the electrodes, soldering or another method known in the art can be used to form the various configurations on the pad 14. The electrodes 24 can have any length and/or width as needed, and spacing between the electrodes 24 can also be sized as needed for a specific application. For example, the width of the electrode tape can be approximately one inch while the spacing between the electrodes 24 can be approximately ½ inch. In one embodiment, the conductive fabric tape is adhered over non-fabric metallic tape. The non-fabric metallic tape can be soldered to electrical leads that are connected to a controller circuit board, such as that shown in FIG. 5, which can be placed under or adjacent to the pad 14. In this way, the electrodes 24 are formed in such a way that the metallic tape picks up the electrical signal from the conductive fabric tape sensing the signals produced by a patient's beating heart when the patient lies on or under the pad. The electrical leads can transfer the signal to the control circuit board for multiplexing, amplification, and filtering as will be described below.

Referring again to FIG. 5, one exemplary ECG circuit board 50 used to implement the ECG amplification and multiplexing circuitry is shown. The circuit board 50 can be about 4 inches by 4 inches, but in other embodiments, a smaller or larger board can be used as needed. The circuit board 50 can consume about 16.2 mA when connected to the output device via a wireless transmission device such as ZigBee, and only about 350 µA when using a direct connection such as USB. In other embodiments, lower-power and lower-range radio transmitters can be used to reduce overall power consumption and extend battery life, as well as other methods and techniques of transmitting ECG information as will be appreciated by those skilled in the art.

The multiplexing network 16, noted above with respect to FIG. 1, can include a series of switches to control which electrodes are used for generating a patient's physiological data. Referring also to the nested L-shaped electrode configuration shown in FIG. 4A, the multiplexing portion of an ECG circuit in communication with the electrodes 24 can select from one of four possible electrodes 24 in each corner of the pad 14, for each of positive and negative inputs 102, 104 shown in FIG. 6, and one of seven possible electrodes for a common/ground input 106. Thus, the two sets of L-shaped electrodes 24 form the pool of possible positive and negative terminals, while the center diagonal electrode 36, along with six of the other electrodes, forms the pool of possible common terminals. The concentric L-shaped electrodes are designed to maximize the probability of finding two electrode contacts on opposite side of the patient's heart regardless of the size and orientation of the patient, so that the optimum ECG signal could be extracted. A series of analog switches, for example the SN74LVC2G66 analog switches, commercial available from Texas Instruments, can control which of the electrodes 24 are connected and can perform all multiplexing operations as the system 10 actively monitors signal quality of the electrodes 24 over time. A person skilled in the art will appreciate that other methods of multiplexing can be implemented to choose which electrodes are sensing the best quality signal.

Figure 6:
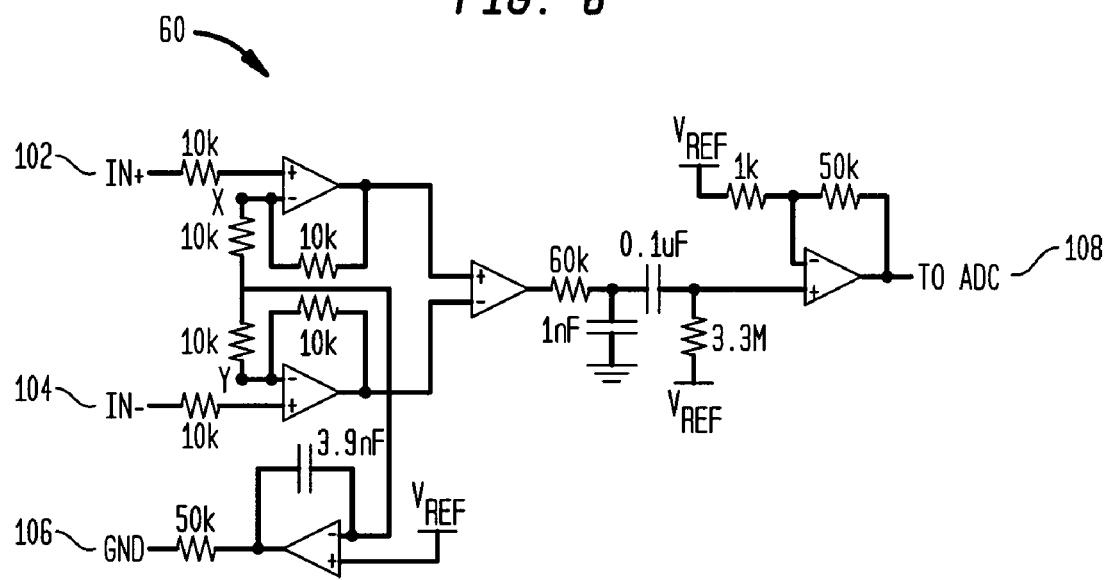
FIG. 6 is a schematic view of one embodiment of an electrocardiogram amplifier and filtering circuit for the system of FIG. 1.

As shown in FIG. 6 and as noted above, a three-lead ECG circuit 60 can be used to improve immunity to 60 Hz background noise and reduce signal processing requirements due to a devoted ground. The three-lead ECG circuit measures a differential signal across two input electrodes and uses feedback via a third electrode (active ground) to cancel the common-mode signal picked up by the two input electrodes 102, 106. An embodiment having this architecture allows the relatively weak ECG signal to be picked up above the stronger 60 Hz background. Alternatively or in addition, a 60 Hz notch filter can be used for a similar purpose.

While various circuit configurations are possible, as further shown in FIG. 6, inputs (In+, In−, Active GND) 102, 104, 106 to an amplifier can come from the multiplexing network 16 while an output 108 can be fed into an analog-to-digital converter (ADC) on a microprocessor 20, for example a MSP430, commercially available from Texas Instruments. The two input signals can be buffered in any way, e.g., by using an operational amplifier such as the OPA340 op-amp, commercially available from Texas Instruments. The differential signal can be amplified in any way, e.g., by using an instrumentation amplifier, for example the INA118 instrumentation amplifier commercially available from Texas Instruments, which can provide a gain of 20 dB, although the circuit can be configured for any desirable gain. A passive resistor and capacitor network can be used to cascade a low-pass filter to a high-pass filter to eliminate high frequency noise and remove DC offset into the previous gain stage. The final amplification stage can use another operational amplifier, such as the OPA340 op-amp, to achieve an additional gain as desired, e.g., 34-40 dB. In one exemplary embodiment, the ECG circuit operates on a 3.3V power supply, although other sources of power can be provided as will be appreciated by those skilled in the art. In an embodiment in which a MSP430 microprocessor is used, an internal +2.5V reference is used to reference the range of the ADC. The reference voltage in the ECG circuit, $V_{REF}$, can be set at +1.25V and can be generated using a resistive divider and buffered using an operational amplifier. Exemplary resistor and capacitor values are shown in FIG. 6, but a person skilled in the art will appreciate that any values can be used as needed in a particular system. A person skilled in the art will also appreciate that various other operational amplifiers, filters, and/or any other circuit elements in any combination can be used to achieve specific results for a specific application.

In one embodiment, a 10-bit multi-channel ADC on board the microprocessor 20 can be used to convert the amplified ECG signal at a 1.6 kHz sampling rate. Higher resolution converters can be used with the selection of a microprocessor with a higher resolution ADC. In addition to the ECG signal, the signals at nodes X and Y in FIG. 6 can also be digitized by the microprocessor to aid in the electrode selection process. The automatic electrode selection algorithm is performed in two steps. The first step determines whether or not the patient is in contact with the selected electrodes and the second step assesses the 'quality' of the acquired ECG signal.

Figure 7:
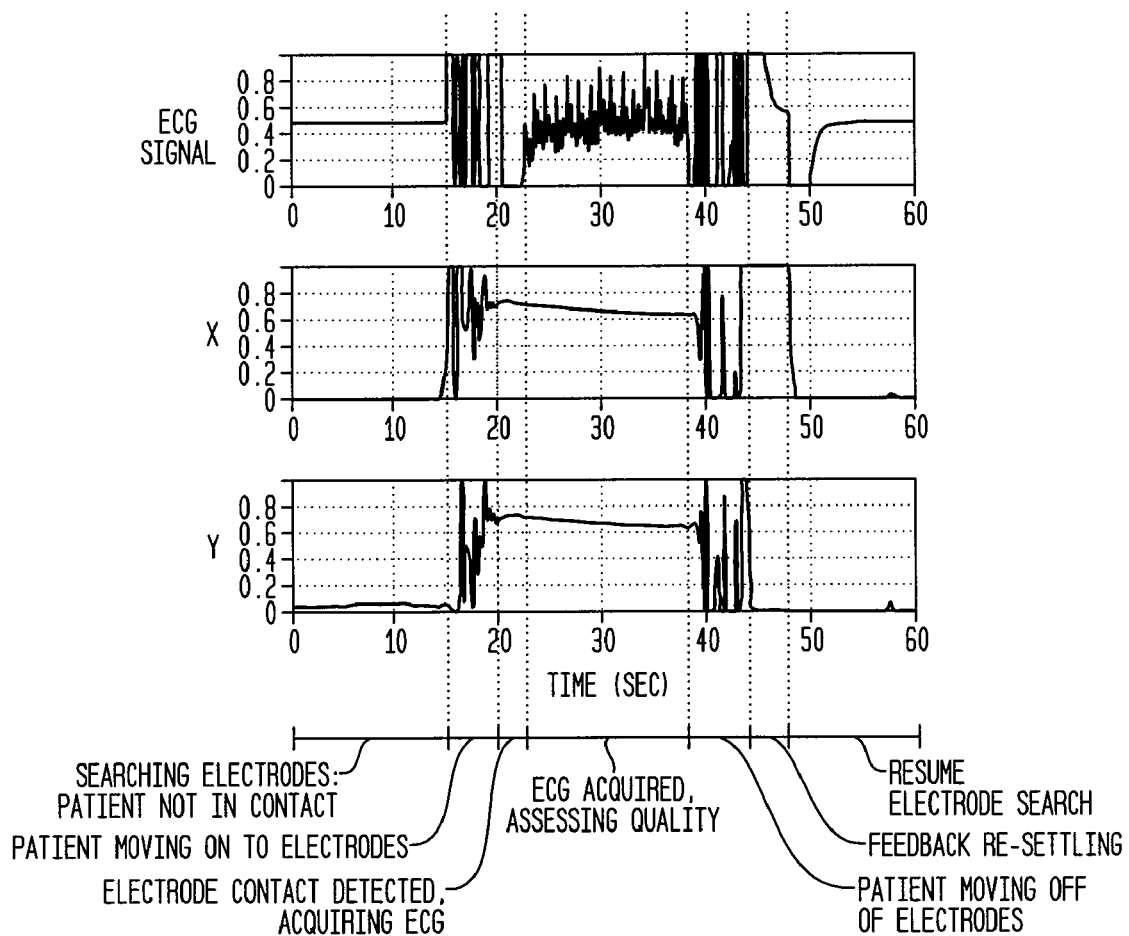
FIG. 7 is a graphical representation of an electrocardiogram acquisition sequence over time for the system of FIG. 1.
Figure 8:
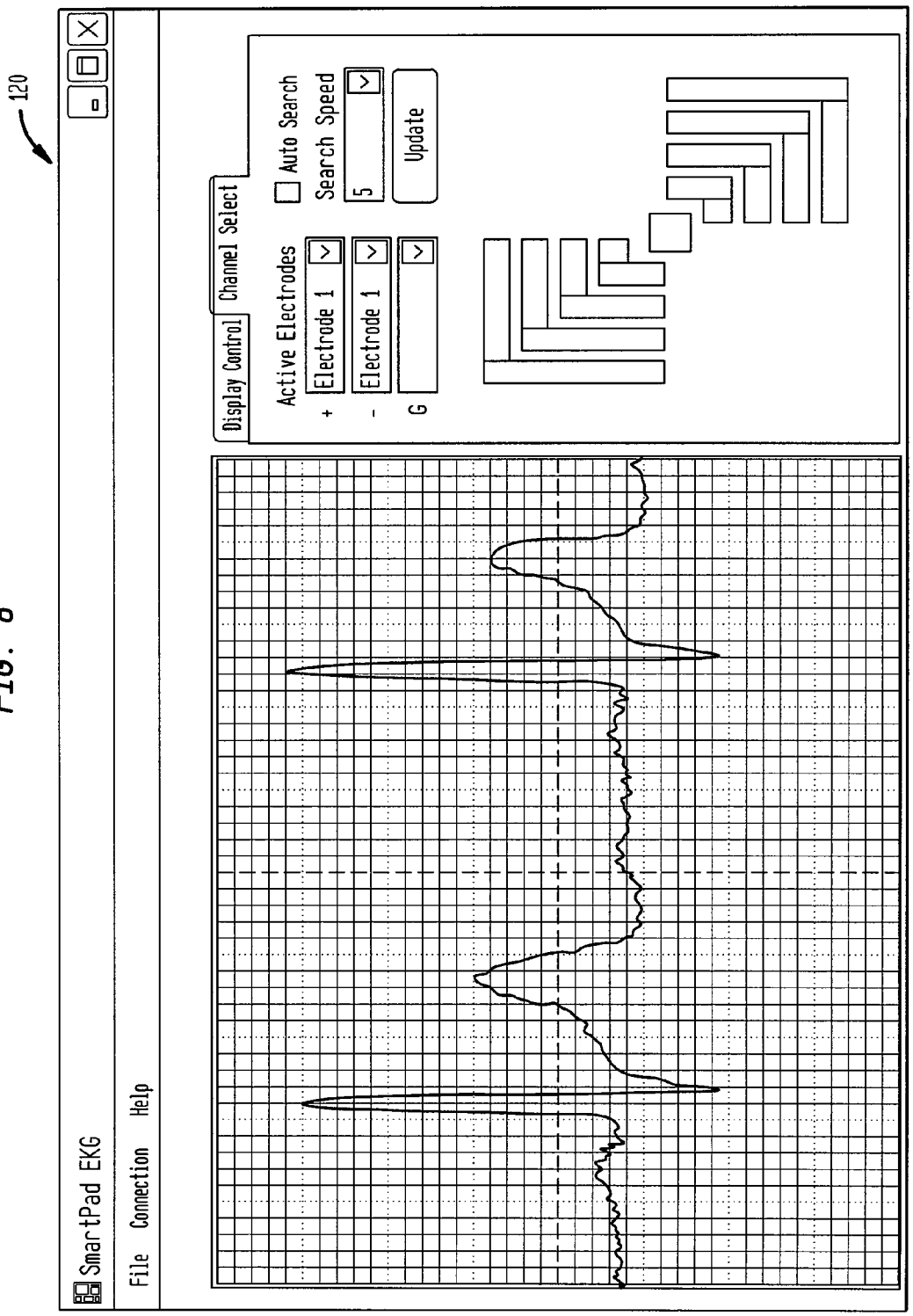
FIG. 8 is a graphical representation of an output display of the system of FIG. 1 showing a patient's electrocardiogram.

FIG. 7 shows a time-lapse graph of the three digitized signals demonstrating a typical ECG acquisition sequence. During the first segment of time, the system is searching for a suitable set of electrodes to use. The system independently cycles through the pool of electrodes for each terminal starting from the inner electrodes. When the patient comes in contact with the selected electrodes, the system detects the patient, stops searching, and begins to acquire the ECG signal.

When the amplifier is functioning properly and the patient is making contact to the selected electrodes, the voltages at nodes X and Y should both be close to or greater than $V_{REF}$, from the circuit shown in FIG. 6, which is the center of the ADC's input range. This can be seen in the middle time segment of FIG. 7. If, for example, the electrode selected for the In+ input is not in contact with the patient, then the voltage at node X will be much lower than $V_{REF}$. If both input electrodes are not in contact with the patient then voltages at both X and Y will be below $V_{REF}$, as shown in the first and last time segments of FIG. 7. By observing the voltages at these two nodes, the system can quickly determine which electrodes in the array are in contact with the patient.

Once the system determines that the patient is making contact with the selected electrodes any number of existing heart-rate detection methods can be used to determine the adequacy of the captured ECG signal. For example, a simple histogram approach coupled with a differentiating heart rate detection scheme can be sufficient. Typically, if the patient is in contact with the electrodes, an ECG signal can be observed. However, if necessary, more complex algorithms can be implemented in real-time using additional hardware.

An important consideration for switching the electrodes and the corresponding high impedance connections to the circuit is to allow sufficient time for the high impedance circuitry to settle. From FIG. 7, it can be seen that once the patient is somewhat stable, the circuitry requires approximately two seconds to respond and settle. In order to limit the number of false negative triggers that might force the system to switch electrodes prematurely (even when there is sufficient contact with the patient), the system is limited to check the signal quality at most every four seconds.

In general, the exemplary systems described herein use a method involving an automatic electrode selection algorithm to acquire a patient's ECG. In one exemplary method, this automatic selection process involves two steps in determining which electrodes to select to generate physiological data. First, the system searches electrode connections until it determines that a patient has come into contact with selected electrodes. Then, the processability and/or quality of the signal acquired is accessed. A variety of attributes can be investigated to determine the processability and quality of a signal. For example, contact between the skin and the electrodes can be considered, as well as a total contact area between the electrodes and the patient. In addition, an examination can be made to ensure that the two ECG electrodes being considered as input signals are located on opposite sides of the heart. Any of these considerations can affect signal reliability, strength, and level of noise within the signal and can influence whether a signal is considered processable.

FIG. 7 illustrates a time-lapse graph of three digitized signals demonstrating an exemplary ECG acquisition sequence. During the first segment of time from time 0 to about time 15, the system is searching for a suitable set of electrodes to use. When a patient comes into contact with electrodes at about time 15 to about time 20, the system detects the patient, stops searching, and begins to acquire the ECG signal from about time 20 to about time 22. When the patient is making contact to the selected electrodes between time 22 and time 38, the voltages at nodes X and Y shown in FIG. 6 are preferably both close to or greater than $V_{REF}$, which is generally the center of the ADC's input range. This can be seen in the middle time segment of FIG. 7 from about time 20 to about time 38. If, for example, the electrode selected for the In+ input 102 is not in contact with the patient, then the voltage at node X will be much lower than $V_{REF}$. If both input electrodes 102, 104 are not in contact with the patient, then voltages at both X and Y will be below $V_{REF}$, as shown in the first and last time segments of FIG. 7. By observing the voltages at these two nodes X and Y, the system can quickly determine which electrodes in the array are in contact with the patient.

Once the system determines that the patient is making contact with the selected electrodes, any number of existing heart-rate detection methods can be used to determine the adequacy of the captured ECG signal. In one embodiment, a simple histogram approach coupled with a differentiating heart rate detection scheme is sufficient. Usually, if the patient is in contact with the electrodes, an ECG signal can be observed. However, if necessary, more complex algorithms can be implemented in real-time using additional hardware to acquire an observable ECG signal. An important consideration for switching the electrodes and the corresponding high impedance connections to the circuit is to allow sufficient time for the high impedance circuitry to settle. As shown in FIG. 7 from about time 20 to about time 22, once the patient is somewhat stable, the circuitry requires approximately two seconds to respond and settle, although more or less time is possible depending on the configuration. In one embodiment, in order to limit the number of false negative triggers that might force the system to switch electrodes prematurely (even when there is sufficient contact with the patient), the system can be limited to check the signal quality every four seconds. As will be appreciated by those skilled in the art, the system can be configured to check the signal quality more or less often depending on specific considerations.

Figure 9:
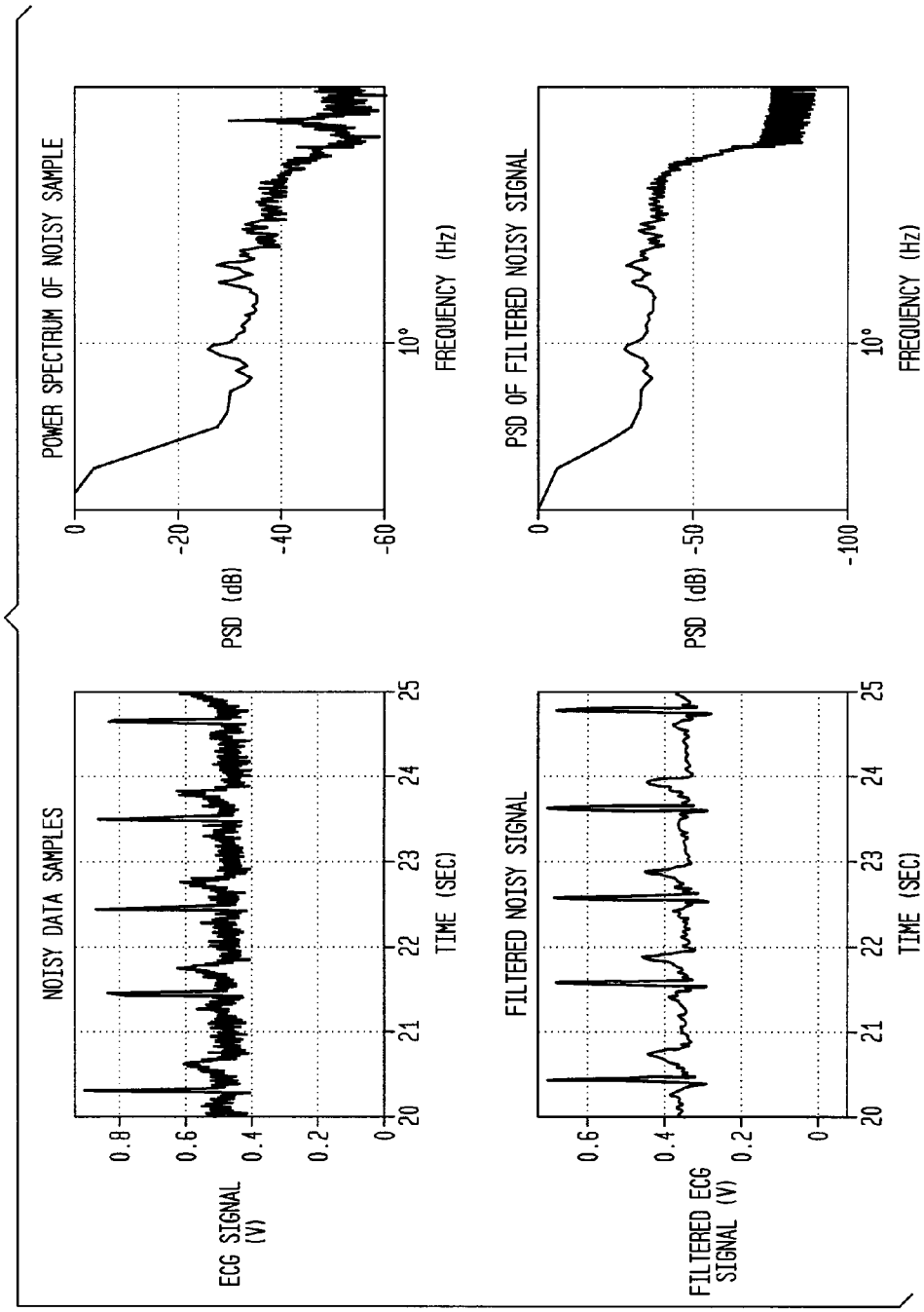
FIG. 9 is a graphical representation of filtering results showing removal of 60 Hz noise from a signal obtained by the system of FIG. 1.

An application for displaying the digitized ECG data and communicating with the multiplexing hardware can be developed using any software program known in the art. In the embodiment shown in FIG. 7, the ECG data is displayed on a display 120 using Visual Basic .NET and is compatible with any PC running Windows. If a cleaner ECG signal is required or other metrics need to be determined, the software can enable the received ECG signal to be saved over a longer period of time and processed with other software tools, such as, for example, MATLAB, commercially available from Mathworks. An example recording of a captured ECG signal using this software is shown in FIG. 9. As seen by the power spectral density (PSD), there is expected electrical noise at 60 Hz. Although the 60 Hz noise may not be enough to impair determination of abnormal heart rhythms, FIG. 9 shows the ECG signal and corresponding PSD, after applying a 32 tap finite impulse response (FIR) filter with a 20 Hz corner frequency, thereby demonstrating another method of suppressing 60 Hz noise without effecting the ECG signal.

Figure 10A:
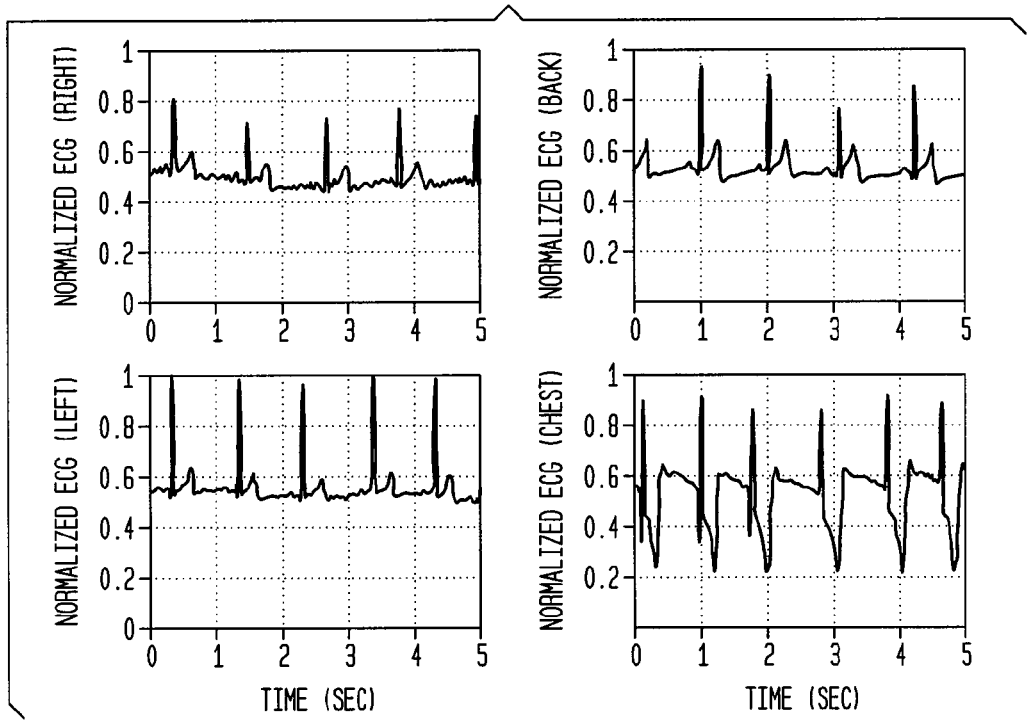
FIG. 10A is a graphical representation of normalized electrocardiogram signals for different patient positions on the pad of FIG. 2.

In one exemplary embodiment, the system can automatically acquire a quality ECG signal as a patient changes positions and orientations on the pad. FIG. 10A shows ECG signals captured while a subject is lying on his right side, back, left side, and chest. As the plots indicate, body position affects both signal amplitude as well as polarity. This is particularly evident in the ECG taken off of the chest. Results when the patient is not vertically aligned with the pad show similar results. Despite the differences, in each case, the signal quality is sufficient and demonstrates that the system is able to extract the patient's ECG regardless of body position or orientation.

Figure 10B:
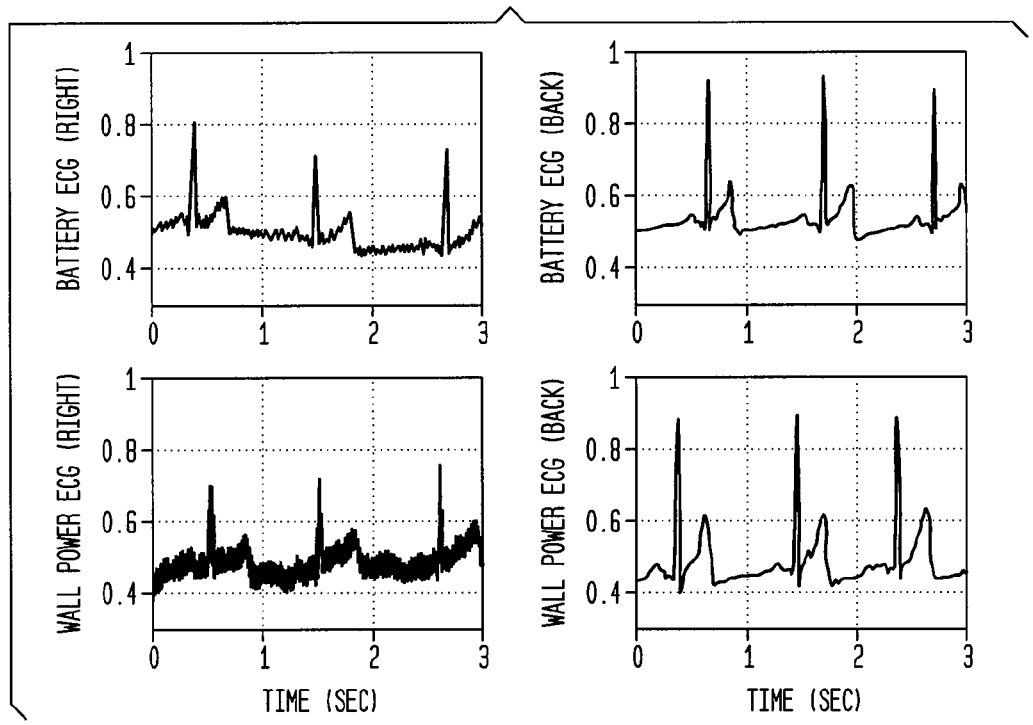
FIG. 10B is a graphical representation of normalized electrocardiogram signals for the system of FIG. 1 using battery power and wall-power.

An advantage to the systems and methods described herein is that the circuit topology and battery powered operation can remove the necessity for a 60 Hz notch filter. To demonstrate the immunity of the design to 60 Hz noise, FIG. 10B shows ECG signals captured while the patient is on his right side and on his back for both the battery-powered and wall-powered cases. As the plots indicate, there is little noise in either of the battery-powered results while the wall-powered result captured from the patient's right side shows a noticeable increase in 60 Hz noise. The difference between results obtained for the right side and results obtained for the back for the wall-powered case is likely due to the body coverage of the electrodes. The electrodes are partially exposed for the prior case, allowing easier pick up of 60 Hz line noise.

As demonstrated herein, systems and methods are provided for unobtrusive and autonomous monitoring of patient physiological parameters. The electrode configurations and detection algorithm presented herein enable hands-free operation on the part of medical personnel and allows for a wireless acquisition system. In addition, any physiological parameter data generated and communicated to the remote output device can be stored and/or recorded on a computer readable medium, for example, floppy diskettes, CD-ROMS, hard drives, flash memory, tape, or other digital storage medium. In some embodiments, physiological data from the controller can be loaded into and/or executed by a computer, or transmitted over any transmission medium known in the art, such as over electrical wiring or cabling, through fiber optics, or via electromagnetic radiation. In some embodiments, the controller and/or output device can be at a location remote from the pad and electrodes. For example, the pad, electrodes, and controller can be located in one room, building, city, or location and the output device can be located in another room, building, city, or location. The controller and/or output device can be configured to communicate wirelessly with all components from a remote location to configure, control, program, and/or otherwise manage any and all aspects of the electrode acquisition sequence described herein. The controller and/or output device can communicate with any other components in a system of the invention using any wireless technology known in the art, including but not limited to, Bluetooth, the IEEE 802.11 standard, Wi-Fi, broadband wireless, and/or any wireless communication that can be accomplished using radio frequency communication, microwave communication, and infrared communication. The controller may utilize point-to-point communication, point-to-multipoint communication, broadcasting, cellular networks, and/or wireless networks. The controller and output device may also utilize wired networks such as local area networks, wide area networks, and/or the Internet.

It is contemplated that the system described herein can be packaged together as a kit or singular unit for use in an ambulance, hospital room, surgical room, in-home application, or any other application as needed. In other embodiments, some, any, and/or all components of the system can be provided separately to work in individualized locations to maximize size and/or efficiency. In any of the embodiments and configurations, any and all components of the system described herein can be single use, disposable, time limited, reconditionable, and/or reusable.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for monitoring patient physiological data, comprising:
   a pad having a plurality of electrical contacts formed thereon in a predetermined pattern, the electrical contacts being configured to sense electrical signals produced by a patient's body;
   a controller in communication with the electrical contacts and configured to select at least two electrical contacts, each sensing a processable electrical signal, and to process a differential signal derived from the processable signals; and
   an output device in communication with the controller for displaying the patient's physiological data based on information processed by the controller;
   wherein the controller is further configured to actively change the selection of the at least two electrical contacts over time by periodically determining which of the plurality of electrical contacts are in contact with the patient and changing the selection of the at least two electrical contacts based on an assessment of the quality of the sensed electrical signals.

2. The system of claim 1, wherein the plurality of electrical contacts comprise strips of conductive material.

3. The system of claim 2, wherein the strips of conductive material are formed into two mirrored sets of nested L-shaped configurations on the pad.

4. The system of claim 2, wherein the strips of conductive material are selected from the group consisting of a nickel/copper polyester fabric and a cloth fabric containing conductive threads.

5. The system of claim 1, wherein at least one of the plurality of electrical contacts is a devoted active ground configured to enable removal of 60 Hz noise from the signal processed by the controller.

6. The system of claim 1, wherein the plurality of electrical contacts are configured to sense electrical signals through the patient's skin to produce physiological data regardless of patient size or patient position on the pad.

7. The system of claim 1, wherein the controller includes a multiplexing network, at least one amplifier, at least one filter, and at least one microprocessor.

8. The system of claim 1, wherein the controller is battery operated.

9. The system of claim 1, wherein the output device is configured to communicate with the controller wirelessly.

10. The system of claim 1, wherein the pad is selected from the group consisting of a gurney pad, a sheet, a warming blanket, and a hospital gown.

11. The system of claim 1, wherein the electrical signals sensed by the plurality of electrical contacts are electrocardiograph signals and physiological data displayed by the output device is an electrocardiograph.

12. The system of claim 1, wherein the controller is further configured to select the at least two electrical contacts such that the at least two electrical contacts span an organ producing the electrical signals.

13. A system for monitoring patient physiological data, comprising:
- a pad having an array of electrodes formed thereon in a predetermined configuration, the pad being configured to be positioned adjacent to a patient's skin; and
- a processor in communication with the pad and configured to select at least two electrodes from the array of electrodes, to process electrical signals received from the at least two electrodes, and to generate physiological data derived from the electrical signals;
- wherein the processor is further configured to actively change the selection of the at least two electrodes over time by periodically determining which of the electrodes from the array of electrodes are in contact with the patient and changing the selection of the at least two electrodes based on an assessment of the quality of the received electrical signals.

14. The system of claim 13, wherein the electrodes of the array of electrodes are selected from the group consisting of strips of conductive tape and cloth fabric made with conductive threads.

15. The system of claim 14, wherein the electrodes of the array of electrodes are formed into mirrored sets of nested L-shaped configurations.

16. The system of claim 14, wherein the electrodes of the array of electrodes are formed from a nickel/copper polyester fabric.

17. The system of claim 13, wherein at least one of the electrodes in the array of electrodes is a devoted active ground configured to enable removal of 60 Hz ambient noise.

18. The system of claim 13, wherein the electrodes are configured to sense electrical signals through the patient's skin to produce physiological data regardless of patient size or patient position on the pad.

19. The system of claim 13, wherein data generated by the processor includes electrocardiograph data.

20. The system of claim 13, wherein the processor is further configured to select the at least two electrodes such that the at least two electrodes span an organ producing the electrical signals.

* * * * *